United States Patent [19]
Schmucker et al.

[11] Patent Number: 6,115,528
[45] Date of Patent: Sep. 5, 2000

[54] RAMAN FIBER OPTIC PROBE ASSEMBLY FOR USE IN HOSTILE ENVIRONMENTS

[75] Inventors: John E. Schmucker, Hurt, Va.; Jon C. Falk, Pittsburgh, Pa.; William B. Archer, Bethel Park, Pa.; Raymond J. Blasi, Harrison City, Pa.

[73] Assignee: The United States of America as represented by the United States Department of Energy, Washington, D.C.

[21] Appl. No.: 09/157,266

[22] Filed: Sep. 21, 1998

[51] Int. Cl.⁷ ...................................................... G02B 6/36
[52] U.S. Cl. .............................. 385/138; 385/12; 356/301
[58] Field of Search ............... 356/301; 385/12, 385/147, 138

[56] References Cited

U.S. PATENT DOCUMENTS

| | | | |
|---|---|---|---|
| 4,573,761 | 3/1986 | McLachlan et al. | 350/96.24 |
| 4,682,846 | 7/1987 | Cowen | 350/96.18 |
| 5,046,854 | 9/1991 | Weller et al. | 356/440 |
| 5,377,004 | 12/1994 | Owen et al. | 356/301 |
| 5,381,237 | 1/1995 | Sela | 356/436 |
| 5,404,218 | 4/1995 | Nave et al. | 356/301 |
| 5,534,997 | 7/1996 | Schrader | 356/301 |
| 5,657,404 | 8/1997 | Buchanan et al. | 385/12 |
| 6,018,389 | 1/2000 | Kyle et al. | 356/301 |

*Primary Examiner*—Hung N. Ngo
*Attorney, Agent, or Firm*—Virginia B. Caress; William R. Moser; Paul A. Gottlieb

[57] ABSTRACT

This invention provides a device for Raman spectroscopic measurement of composition and concentrations in a hostile environment by the use of a first fiber optic as a means of directing high intensity monochromatic light from a laser to the hostile environment and a second fiber optic to receive the lower intensity scattered light for transmittal to a monochromator for analysis. To avoid damage to the fiber optics, they are protected from the hostile environment. A preferred embodiment of the Raman fiber optic probe is able to obtain Raman spectra of corrosive gases and solutions at temperatures up to 600° F. and pressures up to 2000 psi. The incident exciting fiber optic cable makes an angle of substantially 90° with the collecting fiber optic cable. This 90° geometry minimizes the Rayleigh scattering signal picked up by the collecting fiber, because the intensity of Rayleigh scattering is lowest in the direction perpendicular to the beam path of the exciting light and therefore a 90° scattering geometry optimizes the signal to noise ratio.

23 Claims, 3 Drawing Sheets

RAMAN FIBER OPTIC PROBE ASSEMBLY FOR USE IN HOSTILE ENVIRONMENTS

FIELD OF THE INVENTION

The invention relates to the analysis of gases or solutions in a hostile environment and provides an improved fiber optic probe assembly suitable for Raman spectroscopy which is compatible with a hostile high pressure, high temperature or caustic environment.

BACKGROUND OF THE INVENTION

Analyzing or monitoring the composition of gases or solutions in hostile environments such as a chemical reaction inside an autoclave or other suitable pressure vessel or the ambient atmosphere inside a machine pressure vessel frequently requires spectrophotometric techniques based on emission, absorption or scattering processes for qualitative and quantitative analysis. Only optical contact with the gases or solutions of the environment is required.

Frequently the environment is caustic or characterized by high temperature or high pressure and would destroy spectrophotometric analysis equipment such as lasers, filters and monochromators. Therefore the analysis equipment is best placed in a laboratory environment remote from the hostile environment. Probes or cells provide optical connection with the hostile environment and communicate with the analysis equipment via direct light paths or more typically, fiber optic cables. Where measurements must be made at many different locations, a number of probes may be connected to a single piece of remotely-located analysis equipment.

One typical spectrophotometric technique is Raman spectroscopy. When light of a single wavelength interacts with a molecule, the light scattered by the molecule contains small amounts of light with wavelengths different from the incident light. This is known as the Raman effect. The wavelengths present in the scattered light are characteristic of the structure of the molecule, and the intensity of this light is dependent on the concentration of these molecules.

A major difficulty associated with Raman spectroscopy is the low intensity of the Raman scattered light compared to the intensity of the exciting incident light. Additional and intrinsic to the use of fiber optic cables in Raman spectroscopy is the excitation of Raman scattering inside the optical fiber itself (commonly referred to as 'silica scattering'), most notably in the fiber optic cable carrying the exciting high intensity laser light to the probe. Further the intensity of Rayleigh scattered light coming from the sample presents a very large background for the Raman signal. Finally stray light, that is light which is specularly or otherwise reflected back into the collecting fiber, may cause additional noise.

MacLachlan (U.S. Pat. No. 4,573,761), Sela (U.S. Pat. No. 5,381,237), and Schrader (U.S. Pat. No. 5,543,997) teach fiber optic probe heads designed to improve the collection of scattered light from the sample. The probes by Sela and Schrader are of the 180° backscattering type, while the probe by MacLachlan allows for a scattering geometry slightly different from 180°.

MacLachlan's probe identifies a Raman probe that consists of a strand fiber bundle, where the central fiber excites the sample and typically six fibers surround the central fiber to collect the signal. This probe is not strictly of the 180° backscattering type since MacLachlan suggests that the axes of the collecting fibers best make an angle of 10–20° with respect to the axis of the central exciting fiber. The design of the probe, however, does not permit the angle between the axis of the exciting and the axes of the collecting fibers to be much greater than 10–20°. Furthermore MacLachlan states that an angle of convergence beyond 45° essentially reduces the performance of the probe to that of a 180° backscattering arrangement. MacLachlan teaches an adaptation of the probe for insertion in and connection to a process vessel such as a reactor and proposes an appropriate shell with a window made of fused silica, sapphire or diamond. However, the design of the probe is incompatible with high temperatures.

The probe by Sela employing a gradient index lens teaches no adaptation of the design for use in a hostile environment and is not suitable for such applications.

The five probes by Schrader are intended for medical or biological applications and are not suitable for a hostile environment. The fiber optics used in the probes meet no requirements to withstand high temperatures and the window identified as glass, quartz or sapphire is not designed as a high pressure boundary.

Owen (U.S. Pat. No. 5,377,004) gives a comprehensive summary of prior art addressing the problem of silica scattering and Rayleigh scattering and means of filtering these noises. Owen teaches improved optical geometries using lenses, mirrors and optical filters to reduce both noise sources in a 180° backscattering Raman probe. The patent teaches no application of this technology for a hostile environment. In fact the use of lenses, mirrors and optical filters requires that the probe is held near room temperature.

Nave (U.S. Pat. No. 5,404,218) addresses the problem of stray light reaching the collecting fiber (that is light which is specularly or otherwise reflected by the inside of the sample cell) in a 180° Raman backscattering geometry and describes a cell coated on the inside with an anti-reflective layer as well as an optimal cell geometry to reduce the intensity of stray light coming from the walls of the cell. The cell is designed for sampling of possibly caustic gases or solutions as long as the antireflective coating on the inside of the cell is inert with respect to the analyte. The optical fibers used are not identified as being capable of withstanding high temperatures and a fiber optic window identified as sapphire or quartz is optional. However, sapphire and quartz material are subject to caustic corrosion attack and will probably have short useful lifetimes. No high pressure application is proposed. The probe by Nave is only of limited use in a hostile environment.

Weller (U.S. Pat. No. 5,046,854) describes two photometric cells adapted for use in a hostile environment using fiber optic cables and windows made of sapphire, cubic zirconia, diamond, ruby, glass, quartz, Suprasil or Infrasil. Only one of these cells has a design suitable for Raman spectroscopy. The first geometry suggested therein is of the 180° backscattering type. The cell normally includes a mirror at the end face of the cell which is intended to reflect the incident light back into the collecting fiber. Weller, however, suggests that this cell may be adapted for Raman spectroscopy by omitting the mirror at the end face. In the second geometry the excitation laser light is directed straight at the collection fiber optic. This geometry is suitable for absorption spectroscopy, but is the most unfavorable design for any Raman spectroscopy. In a preferred embodiment diamond windows are brazed to the cells to create a pressure boundary, but this seal is likely to crack under thermal cycling.

Cowen (U.S. Pat. No. 4,682,846) describes a hermetic high pressure fiber optic bulkhead penetrator for use in submersible marine equipment, but Cowen makes no reference to a caustic or high temperature environment. The bulkhead penetrator is intended as an optical feedthrough for fiber optics. Nevertheless it could be used for a Raman probe, but no reference to any form of spectrophotometric application is made.

Previous spectrophotometric probes suitable for Raman spectroscopy generally detect light backscattered by 180° into the collecting fiber. This geometry though less optimal is chosen, because it allows for a compact design of the probe. However, in a 180° backscattering geometry Rayleigh scattering received by the collecting fiber is maximized which creates a large noise background for the Raman signal which tends to be orders of magnitude smaller.

These probes are often cells that contain the analyte or are optical fibers pressed against the sample. Some of these probes are designed for use in a hostile environment with windows creating a boundary against a high pressure or caustic environment, but few if any of these cells are suitable at high temperatures.

SUMMARY OF THE INVENTION

This invention provides a device for Raman spectroscopic measurement of composition and concentrations in a hostile environment by the use of a first fiber optic as a means of directing high intensity monochromatic light from a laser to the hostile environment and a second fiber optic to receive the lower intensity scattered light for transmittal to a monochromator for analysis. To avoid damage to the fiber optics, they are protected from the hostile environment. To accomplish this a compact Raman fiber optic probe assembly is provided using an optimal 90° Raman spectroscopy geometry. It enables monochromatic light to penetrate into a hostile environment and scattered light to be collected by means of diamond windows and fiber optic cables. This probe is suitable for hostile high pressure, high temperature, caustic environments.

A preferred embodiment of the Raman fiber optic probe is able to obtain Raman spectra of corrosive gases and solutions at temperatures up to 600° F. and pressures up to 2000 psi. A 90° scattering geometry is utilized which minimizes the Rayleigh scattering received by the collecting fiber.

The incident exciting fiber optic cable makes an angle of substantially 90° with the collecting fiber optic cable. This 90° geometry minimizes the Rayleigh scattering signal picked up by the collecting fiber, because the intensity of Rayleigh scattering is lowest in the direction perpendicular to the beam path of the exciting light and therefore a 90° scattering geometry optimizes the signal to noise ratio, that is the Raman signal against the Rayleigh background. The criterion for the angle formed by the fiber optic cables is that the Raman signal be favored over the Rayleigh background. The substantially 90° angle can be between about 70° and about 110°. Between 85° and 95° is more preferred, and the optimum angle is 90°.

The preferred Raman fiber optic probe comprises a housing and two fiber optic penetrators sealed to the housing by gold metal gaskets. Each fiber optic penetrator holds a metal sheathed fiber optic cable capable of withstanding temperatures of up to 600° F. without thermal degradation. Optical contact with the hostile environment is made through two optical quality diamond windows that transmit the visible light associated with Raman spectroscopy without absorption and with minimal scattering interference. The windows are sealed with gold metal gaskets which are soft enough to create a reliable pressure boundary seal without the danger of straining and breaking the diamond windows during the original assembly of the probe, and which are furthermore reliable under thermal cycling. These sealed diamond windows are impervious to caustic attack, enabling the acquisition of Raman spectra from hot, pressurized and caustic gases or solutions.

One fiber optic cable is used to deliver laser light to the analyte of interest and the other fiber is used to collect the scattered light for transmittal to a monochromator for spectral analysis. The monochromator separates residual Rayleigh noise from the various Raman scattered light bands, thereby enabling the constituent parts of the hostile environment to be identified and their concentrations determined by means of Raman spectroscopic analysis. The monochromator is remotely located from the housing.

In a preferred embodiment this Raman fiber optic probe is that of a dry well assembly, but other adaptations of the probe are obvious for anyone skilled in the art.

DETAILED DESCRIPTION OF THE INVENTION

Figure 1:
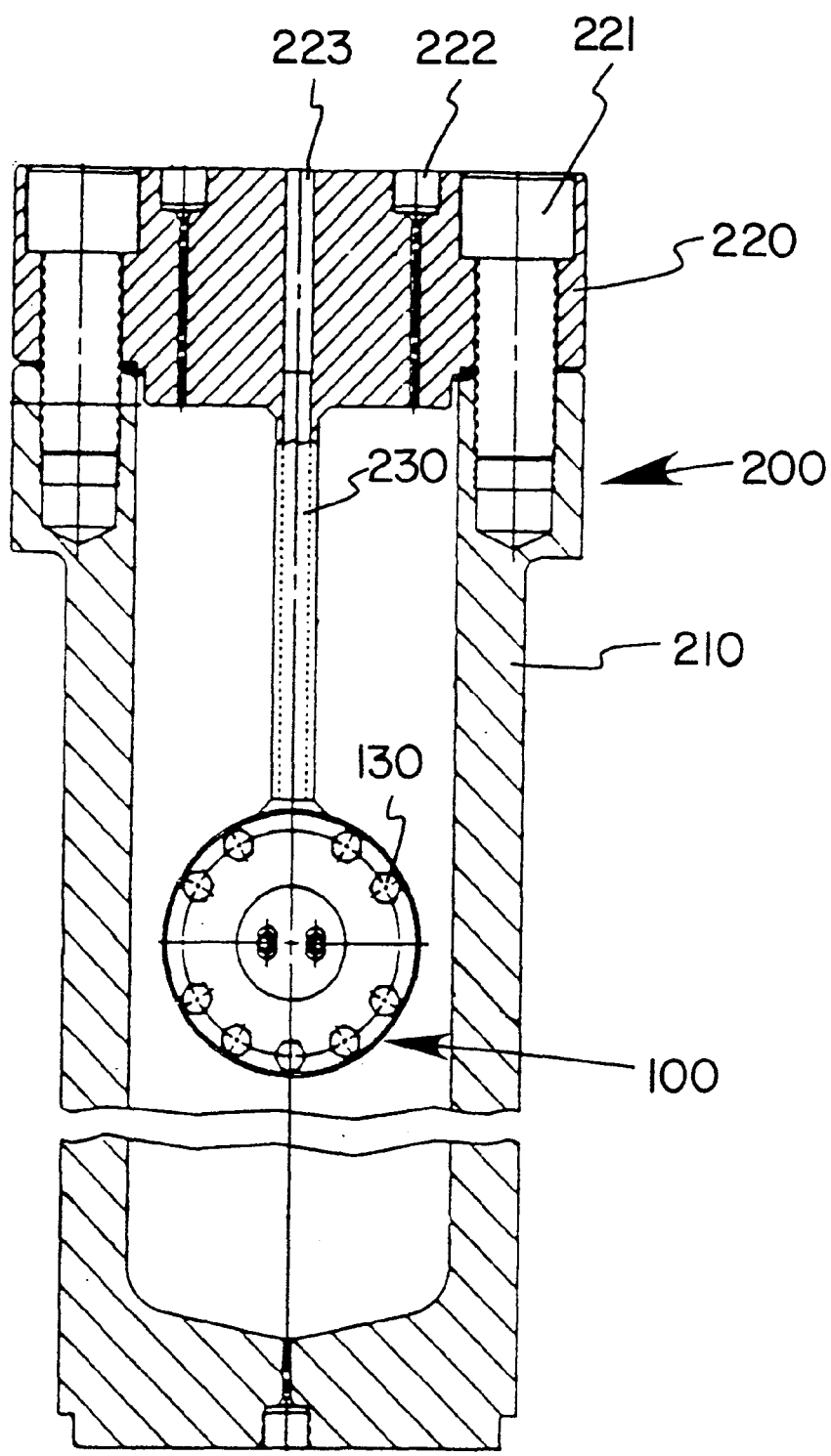
FIG. 1 shows the preferred embodiment of the Raman fiber optic probe assembly in the form of a dry well inside an autoclave

A preferred embodiment of this invention is an improved Raman fiber optic probe assembly for the use in hostile environments in which the probe forms a dry well assembly. FIG. 1 shows an application of the Raman fiber optic probe (Raman probe) inside an autoclave.

In FIG. 1 Raman probe 100 is positioned inside shell 210 of autoclave 200 and supported by hanger pipe 230 from closure head 220 of the autoclave. The inner diameter of the autoclave's shell is about 5 inches. Closure head 220 is attached to shell 210 through bolts 221. The closure head also contains instrumentation ports 222 which may be used for other analysis needs.

In a preferred embodiment the hanger pipe is made of ⅜ inch, Schedule 80 (Extra Strong) pipe. It is welded to base 140, shown in FIG. 2, of the Raman probe and the other side is welded to the underside of closure head 220 such as to create a continuous pipe with the bore of the fiber optic feedthrough 223 of the closure head. Hanger pipe 230 and fiber optic feedthrough 223 provide a pathway for the fiber optic cables connecting Raman probe 100 with the analysis equipment. An incident fiber optic cable transmits the monochromatic laser light to the Raman probe and a collecting fiber optic cable receives the scattered light for transmittal to the analysis equipment.

The internal portions of Raman probe 100 and hanger pipe 230 are at the pressure of the laboratory environment, therefore the Raman probe housing comprising probe base 140 and probe cover plate 130 (refer to FIG. 2) and hanger pipe 230 need to be strong enough to withstand the typically high pressure of the environment inside the autoclave. The choice of materials for the housing of the Raman probe (and the hanger pipe) has to be compatible with the chemical environment of the autoclave which typically contains hot, caustic gases or solutions.

Figure 2:
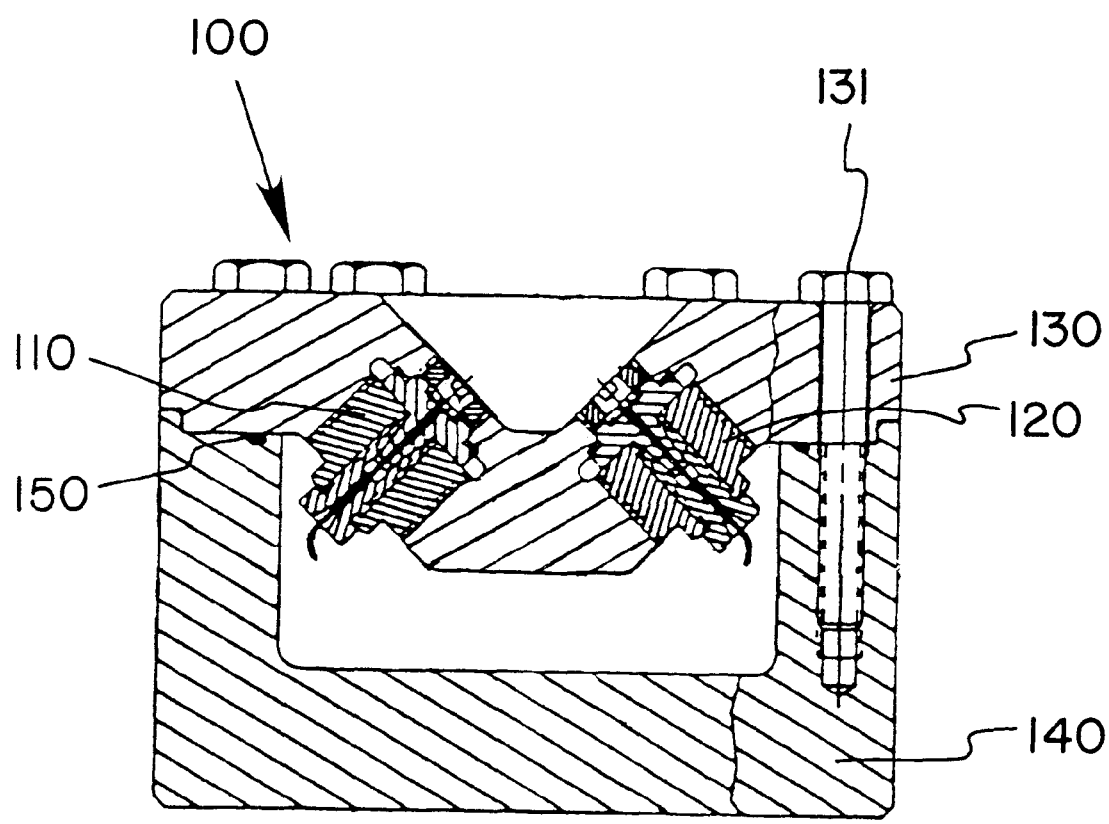
FIG. 2 shows a cross sectional view of the Raman fiber optic probe assembly.

FIG. 2 shows a cross sectional view of Raman probe 100. The housing of the Raman probe comprises probe base 140 and probe cover plate 130. Probe cover plate 130 is bolted to probe base 140 using nine bolts 131 which in a preferred embodiment are ¼–20 UNC hex head bolts, and a seal is made by means of Metal-C-Ring (MCR) 150 which is shown as a black groove in FIG. 2 and extends around the entire circumference of the probe base to probe cover plate mating surface. This MCR makes a reliable seal between the hostile environment on the outside of the housing (the pressure vessel side of the Raman probe) and the inside of the housing (the laboratory side of the Raman probe).

In a preferred embodiment the MCR is made of Inconel Alloy X-750, age hardened and gold plated for corrosion resistance with a pressure rating of 9000 psi. The bolt torque required to seat the MCR is 18–20 in-lbs per bolt. Although the resulting seating pressure is relatively small, the external pressure of the hostile environment supplements the effectiveness of the seal by pressing the walls of the MCR against the mating surfaces of the probe base and probe cover plate.

Probe cover plate 130 is designed to mount two fiber optic penetrators (110 and 120) such that the axes of the fiber optic penetrators form an angle of 90° (see FIG. 2). The first fiber optic penetrator permits monochromatic laser radiation to enter the hostile environment while the second fiber optic penetrator allows the collection of scattered light from the gas or solution under study. For the subsequent discussion it is assumed that fiber optic penetrator 110 accommodates the incident fiber optic cable and that fiber optic penetrator 120 accommodates the collecting fiber optic cable. In a preferred embodiment the design of fiber optic penetrators 110 and 120 is identical. Nevertheless the design or the dimensions of the incident fiber optic penetrator can be different from those of the collecting fiber optic penetrator. It is preferred that the basic design of the fiber optic penetrators is substantially the same. In order to increase the intensity of the collected scattered light, additional collecting fiber optic penetrators could be used. Other combinations of multiple incident and collecting fiber optic penetrators can be used. The axes of these additional collecting fiber optic penetrators also preferably form an angle of 90° with the axes of the incident fiber optic cables.

Figure 3:
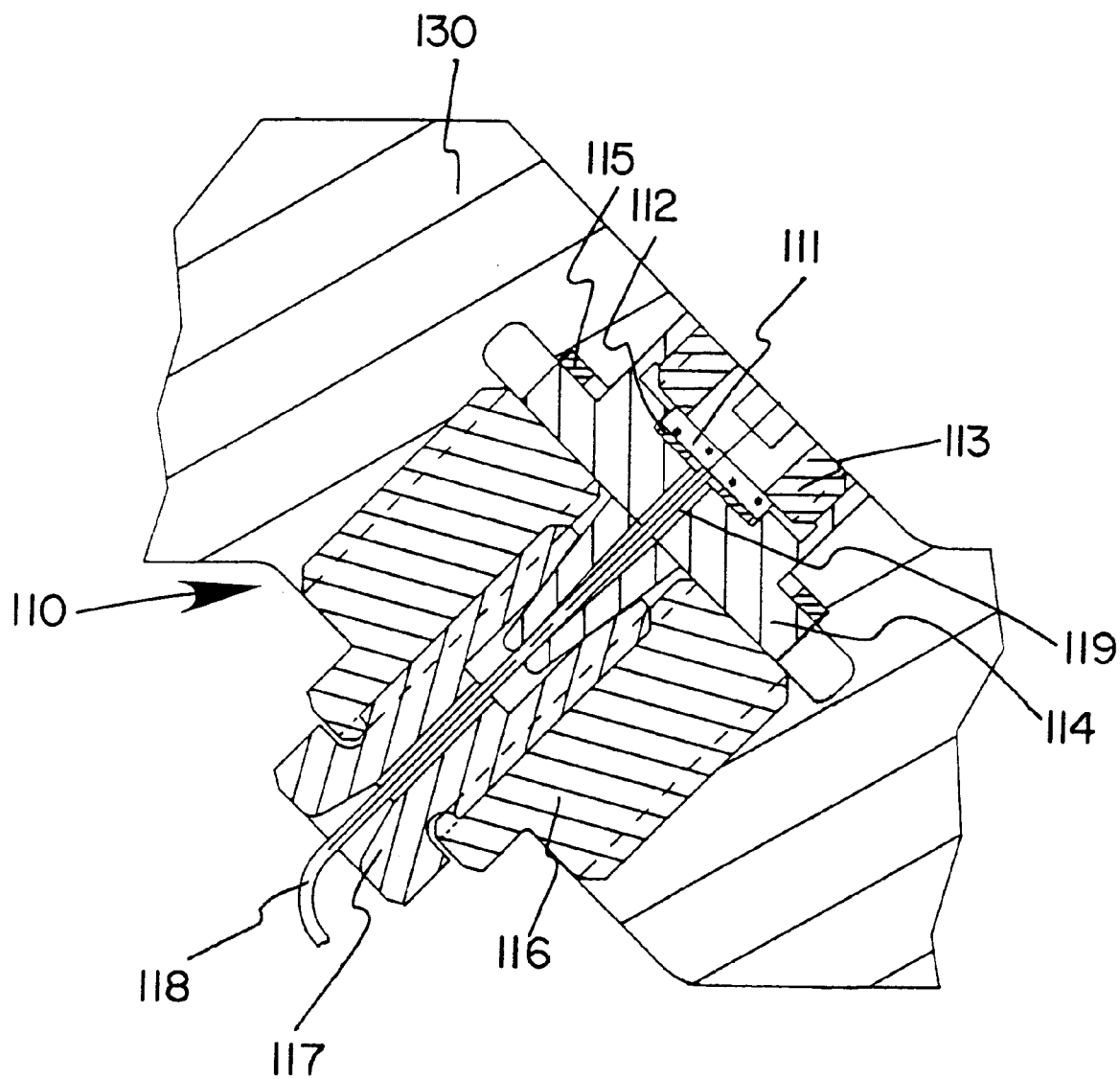
FIG. 3 shows a cross sectional view of the fiber optic penetrator.

The design of the fiber optic penetrators is shown in the example of incident fiber optic penetrator 110 in FIG. 3, which shows the cross sectional view of fiber optic penetrator 110 mounted inside probe cover plate 130.

The design makes use of 1 mm thick industrial diamond window 111, metal sheathed fiber optic cable 118 and gold metal gaskets (112 and 115).

The diamond window forms an optically transparent caustic resistant high pressure boundary through which the incident monochromatic laser light and the Rayleigh and Raman scattered light can pass. Window 111 is seated against window seal 112 on the mating surface of window plug 114. Cylindrical window set plug 113 has a bore to transmit light and has threads to engage window plug 114 and press diamond window 111 against the window seal. In a preferred embodiment the window seal is a 0.015 inch thick gold metal gasket. This seal is impervious to caustic attacks and is soft enough to create a reliable pressure boundary seal. The seal remains reliable even under heavy thermal cycling to which the Raman probe may be exposed. Excellent sealing is achieved without requiring large set screw torque values which could strain and break the window during assembly of the window plug. In a preferred embodiment the window is made of diamond, which is resistant to caustic corrosion and is sufficiently strong to form a high pressure optical barrier. The window mating surface on window plug 114 has a surface finish of 8 rms or better to ensure effective seating of window seal 112.

Metal sheathed fiber optic cable 118 is inserted into a bore in window plug 114 and is abutted against window 111. The window plug extends into a collet which allows fiber optic cable 118 to be clamped as described below and secures the fiber optic cable in its position. The space 119 in the bore of the window plug is filled with high temperature, optical quality epoxy glue to further affix the fiber optic cable against the window. The epoxy glue chosen is capable of sustaining its adhesive and optical transmission characteristics at the temperature of the hostile environment.

Window plug assembly 114 seals against probe cover plate 130 with window plug seal 115. In a preferred embodiment this is a 0.030 inch thick gold metal gasket. The mating surfaces on the probe cover plate and the window plug have a surface finish of 8 rms or better to ensure effective seating of window plug seal 115. To prevent window plug 114 from turning and causing damage to gold metal gasket 115 and twisting fiber optic cable 118, flats have been provided on the outside diameter of the window plug and mating surfaces in the 0.505 diameter hole in probe cover plate 130.

The window plug is sealed by installing and seating cell plug 116 with the torque necessary to obtain the required seating load on window plug seal 115. Cell plug 116 is a cylinder with a bore. Cell plug 116 is threaded both in the bore and on the outside. Crimp nut 117 screws into the threaded bore of cell plug 116 and pinches the collet of the window plug to prevent separation of the fiber optic cable from the diamond window due to tension being applied to the cable. Cell plug 116 and crimp nut 117 together comprise a probe plug.

The design of window plug 114 that holds the diamond window, and seating of the window plug using threaded cell plug 116 and crimp nut 117, has been successfully tested. An advantage of this design is its ease of assembly and reliability. The use of gold metal gaskets results in secure pressure seals which are impervious to caustic attack. The seating of the 1 mm diamond window which forms a boundary against pressures of up to 2000 psi with a gold metal gasket is superior to other designs (for example where the window is brazed to the metal) because of its simple assembly and reliability under thermal cycling. The use of a metal sheathed fiber optic cables and high temperature optical quality epoxy make this assembly suitable at temperatures of up to 600° F.

In application, calibration of the Raman fiber optic probe is required prior to installation. Each Raman probe has slightly different signal characteristics based on the unique materials of construction and assembly fit up. Features affecting the Raman signal output of the probe include: (1) the exact geometry of the probe including the alignment of the fiber optic cables and the diamond windows, (2) the light transmission characteristics of the fiber optic cables, optic glue and diamond windows used, (3) the length of the fiber optic cables between the Raman probe and the analysis equipment, and (4) the use of filters or lenses in the incident or collecting beam path.

Ideally the calibration method only requires standard temperature and pressure values instead of the high operating temperatures and pressures. However, the Raman signal output undergoes spectral changes as a function of temperature. Therefore at least one calibration at elevated temperatures is indicated. Additionally spectra at different pressures may also be acquired. A computer program can then be used to extrapolate to other temperatures (or pressures) to establish the spectral efficiency.

A typical example for the use of the Raman fiber optic probe is the measurement of hydrogen in a process room to warn of the danger of deflagration. The first step in a calibration method is to immerse the Raman probe in a volume of pure hydrogen at standard temperature and pressure conditions and to obtain a spectrum from the Raman probe output signal. Subsequent steps consist of obtaining spectra from the Raman probe for known concentrations of hydrogen at various pressure and temperature conditions. The spectral intensity varies proportionally with the hydrogen gas concentration and the temperature. The spectral intensity data is then correlated with the operating data and the calibration is completed by establishing a calibration table calculated from these data points.

We claim:

1. A Raman fiber optic probe assembly for use in a hostile environment comprising:
   a probe housing having a pressure vessel side adapted to be in contact with said hostile environment and a laboratory side adapted to be in contact with a non-hostile environment;
   an incident fiber optic penetrator adapted to penetrate and seal to said housing having a pressure vessel portion and a laboratory portion and having an incident window positioned to allow optical access to said pressure vessel side of said housing, said incident fiber optic penetrator adapted to mount an incident fiber optic cable in said laboratory portion, said incident fiber optic cable being optically connected to said incident window;
   a collecting fiber optic penetrator adapted to penetrate and seal to said housing having a pressure vessel portion and a laboratory portion and having a collecting window positioned to allow optical access to said pressure vessel side of said housing, said collecting fiber optic penetrator adapted to mount a collecting fiber optic cable in said laboratory portion, said collecting fiber optic cable being optically connected to said collecting window;
   said incident fiber optic penetrator and said collecting fiber optic penetrator positioned in said housing such that the axis of the incident fiber optic cable and the axis of the collecting fiber optic cable form an angle of substantially 90°.

2. The probe assembly of claim 1 wherein said angle is between 70° and 110°.

3. The probe assembly of claim 2 wherein said angle is between 85° and 95°.

4. The probe assembly of claim 3 wherein said angle is 90°.

5. The probe assembly of claim 1 wherein said incident and collecting fiber optic penetrators each comprises:
   a window plug having said incident or collecting window sealed thereto, having a bore therein to receive a fiber optic cable and to position said cable abutting said window, and having a gasket seat for positioning a gasket between said window plug and said housing to seal said penetrator to said housing; and
   a cell plug abutting said window plug and adapted to be engaged with said housing to push said window plug against said gasket, said cell plug having a bore therein to accommodate said cable.

6. The probe assembly of claim 5 wherein each window plug further comprises a collet extending therefrom into said bore of said cell plug for holding said cable.

7. The probe assembly of claim 6 wherein each penetrator further comprises a crimp nut engaged in said bore of said cell plug and having a bore therein to accommodate said cable, and wherein said crimp nut surrounds and pinches said collet.

8. The probe assembly of claim 5 wherein each of said windows is sealed to said window plug with a gasket positioned therebetween.

9. The probe assembly of claim 8 wherein each of said penetrators further includes a window set plug abutting said window and engaged with said window plug to push said window against said gasket.

10. The probe assembly of claim 8 wherein each of said gaskets is gold.

11. The probe assembly of claim 10 wherein each of said windows is a diamond window.

12. The probe assembly of claim 5 wherein said cell plug is engaged in said housing by threads on the exterior of said cell plug.

13. The probe assembly of claim 7 wherein said cell plug is engaged in said housing by threads on the exterior of said cell plug.

14. The probe assembly of claim 13 wherein said crimp nut is engaged in said cell plug by threads on the exterior of said crimp nut and threads in the bore of said cell plug.

15. An assembled probe assembly comprising the probe assembly of claim 1 and further comprising:
   an incident penetrator gasket positioned between said incident penetrator and said housing;
   a collecting penetrator gasket positioned between said collecting penetrator and said housing;
   an incident fiber optic cable mounted in said incident fiber optic penetrator and abutting said incident window: and
   a collecting fiber optic cable mounted in said collecting fiber optic penetrator and abutting said collecting window.

16. The assembled probe assembly of claim 15 further including epoxy disposed between each of said optic fiber cables and said windows.

17. The assembled probe assembly of claim 15 wherein each of said penetrator gaskets is gold.

18. The assembled probe assembly of claim 15 wherein each of said fiber optic cables is a metal sheathed cable.

19. An assembled probe assembly comprising the probe assembly of claim 7 and further comprising:
   an incident penetrator gasket positioned in said gasket seat of said cell plug of said incident penetrator;
   a collecting penetrator gasket positioned in said gasket seat of said cell plug of collecting penetrator;
   an incident fiber optic cable mounted in said collet of said window plug of said incident fiber optic penetrator and abutting said incident window: and
   a collecting fiber optic cable mounted in said collet of said window plug of said collecting fiber optic penetrator and abutting said collecting window.

20. The assembled probe assembly of claim 19 wherein each of said windows is sealed to said window plug with a gasket positioned therebetween, and wherein each of said penetrators further includes a window set plug abutting said window and engaged with said window plug to push said window against said gasket.

21. The assembled probe assembly of claim 15 wherein said hostile environment has a temperature up to 600° F.

22. The assembled probe assembly comprising the probe assembly of claim 21 wherein said hostile environment has a pressure up to 2000 psi.

23. The assembled probe assembly comprising the probe assembly of claim 15 wherein said hostile environment has a pressure up to 2000 psi.

* * * * *